(12) United States Patent
Jousma et al.

(10) Patent No.: US 8,572,790 B2
(45) Date of Patent: Nov. 5, 2013

(54) POWER DENTAL CLEANING APPLIANCE WITH ACTUATOR SYSTEM FOR PRODUCING A SHORT BRISTLE STROKE

(75) Inventors: Hendrik Richard Jousma, Groningen (NL); Michiel Allan Schallig, Drachten (NL); Willem Sjoerd Dijkstra, Witmarsum (NL)

(73) Assignee: Koninklijke Philips N.V., Eindhoven (NL)

( * ) Notice: Subject to any disclaimer, the term of this patent is extended or adjusted under 35 U.S.C. 154(b) by 167 days.

(21) Appl. No.: 13/141,792

(22) PCT Filed: Dec. 4, 2009

(86) PCT No.: PCT/IB2009/055522
§ 371 (c)(1),
(2), (4) Date: Jun. 23, 2011

(87) PCT Pub. No.: WO2010/076696
PCT Pub. Date: Jul. 8, 2010

(65) Prior Publication Data
US 2011/0258793 A1    Oct. 27, 2011

Related U.S. Application Data

(60) Provisional application No. 61/141,357, filed on Dec. 30, 2008.

(51) Int. Cl.
*A46B 13/00* (2006.01)
(52) U.S. Cl.
USPC .............................. 15/22.1; 15/22.2; 15/167.1
(58) Field of Classification Search
USPC ..................... 15/22.1, 22.2, 167.1, 201, 186
See application file for complete search history.

(56) References Cited

U.S. PATENT DOCUMENTS

| 4,346,492 A | 8/1982 | Solow |
| 4,795,347 A | 1/1989 | Maurer |
| 5,327,608 A | 7/1994 | Kosakewich |
| 5,623,746 A | 4/1997 | Ichiro |
| 5,974,615 A | 11/1999 | Schwarz-Hartmann et al. |

(Continued)

FOREIGN PATENT DOCUMENTS

| CN | 1520788 A | 8/2004 |
| DE | 102005009965 A1 | 12/2006 |

(Continued)

*Primary Examiner* — Shay Karls

(57) ABSTRACT

One embodiment of an actuator system for a power dental cleaning appliance to produce a tapping motion of bristle tufts in a dental cleaning appliance includes a plurality of piston elements (16) mounted in a brushhead for movement away from and then toward the brushhead (12). Bristle tufts (20) are positioned on the piston elements and move sequentially against and away from the teeth to produce a cleaning action. A low frequency fluid pressure action (40) in the range of 1-6 Hz maintains conformity of the bristle tufts in a low frequency sequence against the teeth, while a higher frequency fluid pressure action (42) in the range of 100-300 Hz moves the bristle tufts at that frequency to produce a tapping bristle action on the teeth to produce cleaning. In another embodiment, an actuation system includes an elongated actuator member (52) made of elastic material which expands and contracts about its longitudinal axis at a selected frequency by fluid pressure. A plurality of actuator sections (56) are fixedly mounted on the actuator element. The actuator sections are configured such that as the actuator member expands, an upper bridge portion (63) of the actuator section moves upwardly. The bristle tufts (74) mounted thereon produce a cleaning action on the teeth.

15 Claims, 4 Drawing Sheets

(56) References Cited

U.S. PATENT DOCUMENTS

| | | |
|---|---|---|
| 6,450,178 B1 | 9/2002 | Clay |
| 6,568,020 B1 | 5/2003 | Hosokawa |
| 2003/0079305 A1 | 5/2003 | Takahata et al. |

FOREIGN PATENT DOCUMENTS

| | | |
|---|---|---|
| DE | 102005009958 A1 | 1/2007 |
| EP | 0628291 A2 | 12/1994 |
| WO | 2006067749 A2 | 6/2006 |
| WO | 2007024829 A2 | 3/2007 |
| WO | 2007096167 A1 | 8/2007 |

POWER DENTAL CLEANING APPLIANCE WITH ACTUATOR SYSTEM FOR PRODUCING A SHORT BRISTLE STROKE

This invention relates generally to power dental-cleaning appliances which utilize a bristle action directly toward and away from the teeth, i.e. approximately perpendicular to the teeth, and more specifically concerns such an appliance which operates within selected ranges of frequency and bristle stroke.

It is known that a tapping/light hammering action of bristles against teeth surfaces can produce effective cleaning of teeth, including interdental regions. But the effectiveness of such appliances depends upon a relatively short bristle stroke, as well as a certain frequency range, to produce effective results. Fluid (gas or liquid) pressure actuators have certain design advantages in such an appliance relative to other types of actuators, but the effect of cavitation in liquid caused by the actuator prevents effective movement of the bristle tuft field at frequencies above 80 Hz. Effective cleaning typically requires a frequency in the range of 100-300 Hz.

Accordingly, it is desirable to have a fluid pressure actuator which can produce a bristle tapping action with an effective stroke length and a frequency within a desired range, e.g. 100-300 Hz.

One embodiment of a dental cleaning appliance comprises: an appliance body having a brushhead portion with a plurality of movable piston members mounted therein for in-and-out movement thereof toward and away from the teeth when a distal end of the brushhead portion is positioned in the mouth; bristle tufts mounted on the piston members, for cleaning contact with the teeth; a low frequency actuator for moving the piston members at a low frequency to generally sequentially conform tips of the bristle tufts to the teeth; and a higher frequency actuator for moving the piston members at a higher frequency relative to the teeth to produce cleaning of the teeth by periodic contact between the bristle tufts and the teeth.

Another embodiment comprises: an appliance body, including a driving system having an elastic elongated actuator member which expands and contracts about its longitudinal axis at a selected frequency; a plurality of actuator sections fixedly mounted on the actuator member, each actuator section being configured so that as the actuator member expands, an upper portion of the actuator section moves upwardly; and bristle tufts mounted on the upper portion of each actuator section such that as the actuator member expands, the upper portion of the actuator section and the bristle tufts mounted thereon move alternately outwardly and then back, toward and away from the teeth when the appliance is positioned in the mouth.

Figure 1:
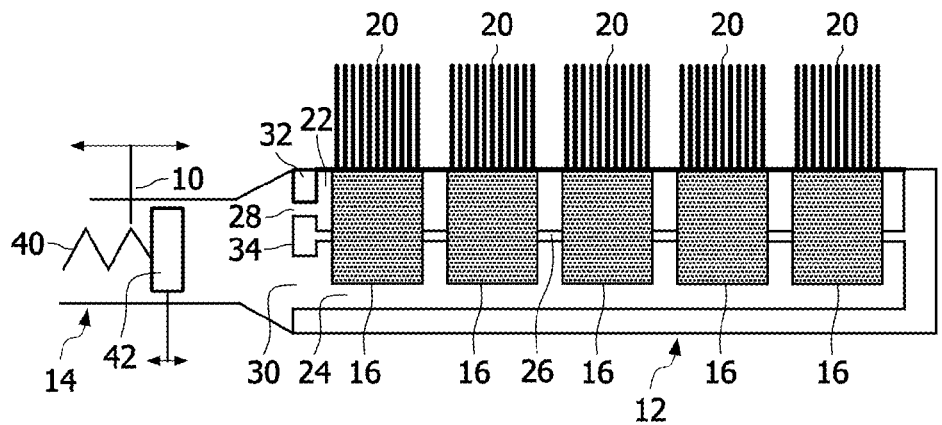
FIGS. 1-3 are cross-sectional diagrams of three operational states of a portion of a dental appliance, showing a first fluid pressure actuator embodiment.
Figure 2:
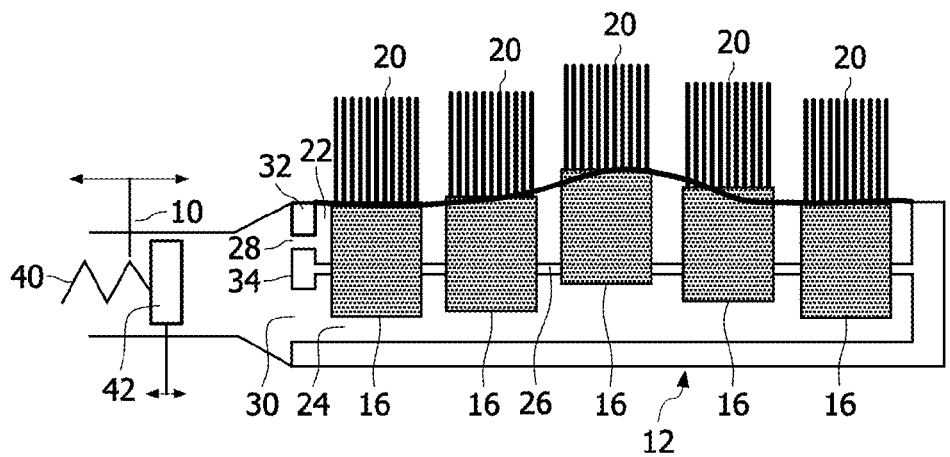
Figure 3:
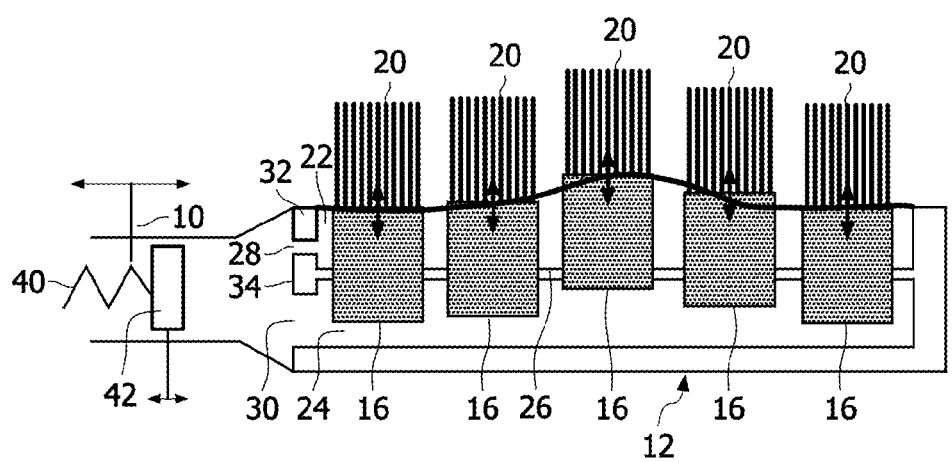

FIGS. 1-3 show one embodiment of an actuator assembly and brushhead assembly in a dental appliance. The actuator assembly 10 and brushhead assembly 12 are positioned in an appliance housing portion 14. A plurality of pistons 16-16 are mounted for up/down movement in the brushhead assembly. Housing 14 and the pistons 16 are typically made from a plastic material. In one embodiment, there are a total of five separate pistons, but this number can vary.

Mounted on the upper surface of each piston 16-16 are a plurality 20 of bristle tufts. Typically, each piston will have a number of bristle tufts, in the range of five or more. Each bristle tuft will contain approximately 90 bristles or filaments which can vary in size, configuration and material. In one embodiment, the bristles/filaments will have a diameter of 6 mil and will extend approximately 8 mm from the top of the piston.

Housing 14 includes two fluid channels 22 and 24. Fluid channels 22 and 24 are defined by housing walls and an interior housing member 34 which extends for the length of the housing. Entrance to fluid channels 22, 24 at the proximal end of the brushhead assembly is through flow openings 28 and 30. Flow opening 28 is narrow, approximately 1 mm wide in the embodiment shown. Flow opening 28 extends for the full width of the housing. Flow opening 30 is larger, approximately 3 mm wide and also extends for approximately the full width of the brushhead. Flow openings 28 and 30 are defined by flow header elements 32 and 34 which are part of housing 14. Flow header element 32 extends downwardly from the upper wall of the housing, while flow header element 34 is positioned at the proximal end of interior member 34. The size of the flow openings can be varied to some extent, depending upon the desired action of the brushhead, although one opening must be quite narrow and the other one larger.

Positioned toward the rear of housing 14 in FIG. 1 are a low frequency spring member actuator 40 and a higher frequency actuator assembly 42 which in one embodiment is a linear actuator operating on a piston element which is in fluid-tight contact with the interior surface of housing 14. A fluid such as water is present in housing 14 forward of the piston member. Spring member 40 and the higher frequency actuator assembly 42 operate on the fluid to produce the up-and-down motion of the brushhead pistons 16 and hence the bristle tufts 20 mounted thereon. Spring member 40 produces a low frequency fluid pressure action, preferably within the range of 1-6 Hz, although it could be slightly higher, while the higher frequency actuator assembly 42 produces a higher frequency fluid pressure action, within the range of 100-300 Hz. Hence, there is a combined low frequency/high frequency action on the fluid within the housing, with the high frequency action superimposed on the low frequency action.

FIG. 1 shows the appliance in a null position, i.e. the system is not operating, wherein all the pistons 16 are in the same neutral position, with the tips of the bristle tufts being co-planar. FIG. 2 shows the bristle action due to the low frequency action of the spring member 40, with fluid being forced through narrow opening 28. The low frequency (1-6 Hz) fluid action results in the bristles conforming/adjusting to the oral geometry, i.e. the bristle tufts move with a low frequency in such a manner that the bristle tufts on the respective individual pistons are moved sequentially against the teeth for a relatively long period of time. Each of the bristle tufts in turn contacts and remains in contact with the teeth in accordance with the frequency of the low frequency actuator.

The higher frequency fluid pressure action (100-300 Hz) produced by the linear actuator/piston assembly 42 is superimposed on the low frequency fluid pressure action provided by the spring member 40. This higher frequency action produces a frequency of movement of the bristle tufts between 100-300 Hz. Fluid producing the higher frequency action moves through the wider flow opening 30, resulting in an effective tapping action of the bristle tufts, as shown in FIG. 3, by virtue of the fluid in the higher frequency fluid channel operating on the pistons 16. The piston action is in the frequency range of 100-300 Hz and produces a tapping or light hammering action of the bristle tufts against the teeth, resulting in effective cleaning of the teeth.

Hence, in this embodiment, the combination of low frequency and higher frequency fluid action results in an effective cleaning with a short bristle tuft stroke. The bristle tuft stroke in this case is short because the higher frequency movement of the bristle tufts begins with the bristles substantially in contact with the teeth; they first move away from the teeth during the first half-cycle of the higher frequency fluid action, and then back to contacting the teeth in the other half-cycle with a tapping/light hammering action. In the neutral position the bristles are generally conforming to the teeth instead of being away from the teeth. This results in a shorter stroke for the bristle tufts, which is valuable in a limited space, and also permits the bristles to more readily reach into remote areas of the teeth, i.e. interproximal areas.

Figure 4:
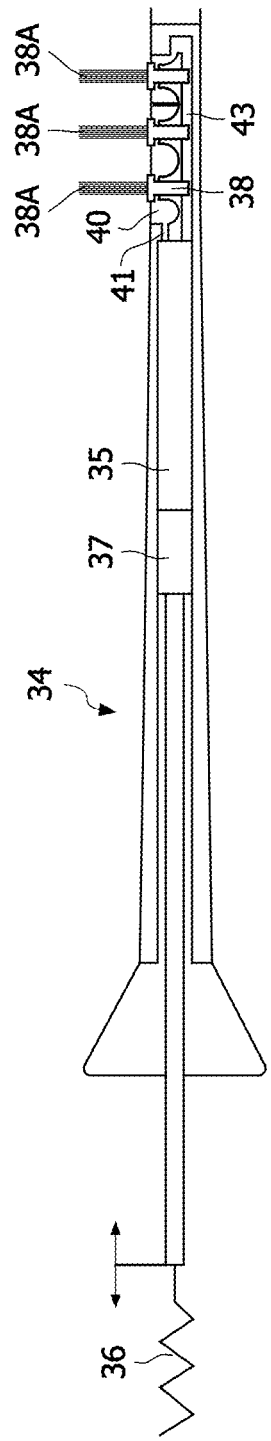
FIGS. 4-6 are various views of another fluid pressure actuator embodiment.
Figure 5:
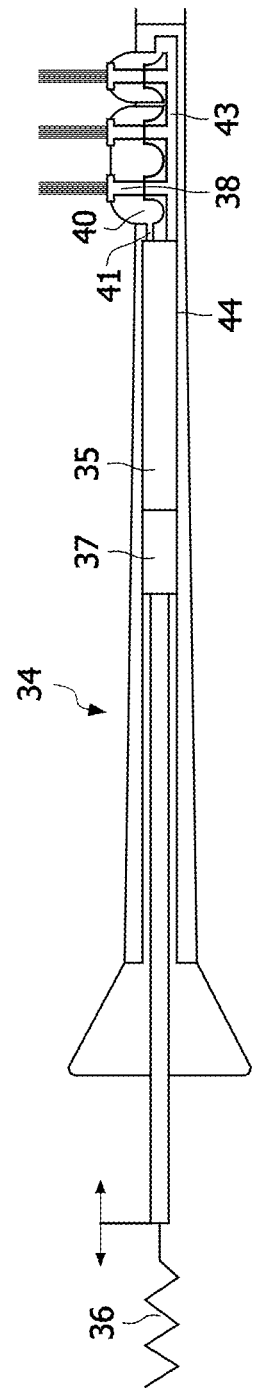
Figure 6:
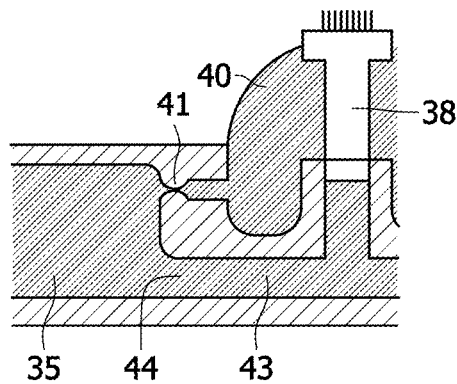
Figure 7:
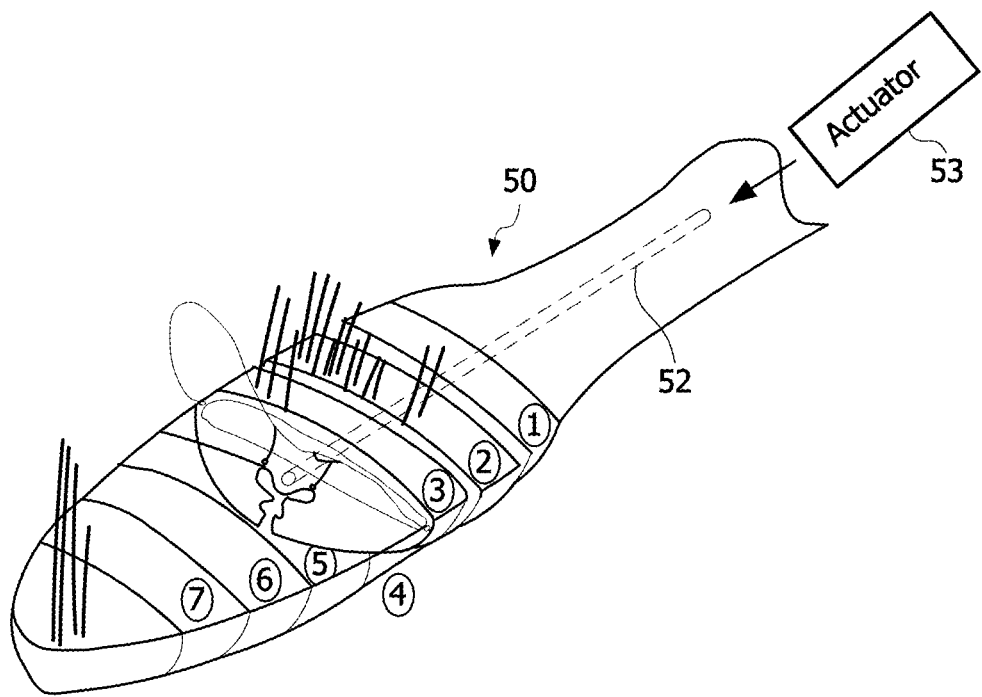
FIGS. 7-10 are various views of still another fluid pressure actuator embodiment.

FIGS. 4-6 show a variation of the above embodiment. It includes a brushhead housing 34 with an internal fluid channel 35, with fluid such as water to the right of a piston member 37. A spring actuator 36 provides the low frequency fluid action, while a linear actuator operating on a piston element 37, such that it moves back and forth in channel 35 to provide the high frequency fluid action. The brushhead includes a plurality of piston members 38, on which a plurality of bristle tufts 38A are mounted. The embodiment includes a first fluid portion 40 with a narrow entrance 41 and a second fluid portion 43 with a larger entrance 44. Fluid moves into the first fluid portion 40 through narrow entrance 41 by action of the low frequency spring member (1-6 Hz), while fluid moves into the second portion 43 through the larger entrance 44 by action of the higher frequency actuator (100-300 Hz;). The low frequency action generally conforms the bristle tips to the surfaces of the teeth, while the higher frequency action produces the higher frequency tapping action of the bristle tufts against the teeth, producing the cleaning action. The two fluid actions are thus in effect superimposed.

Figure 8:
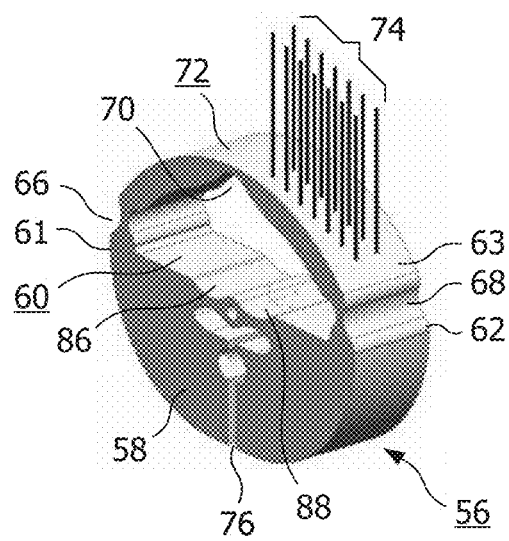
Figure 9:
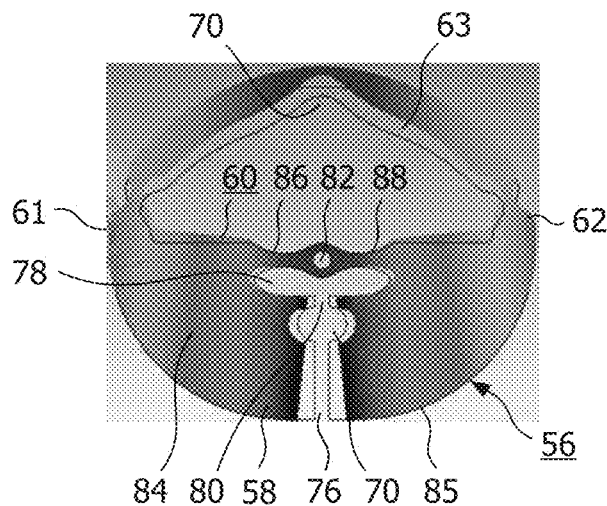
Figure 10:
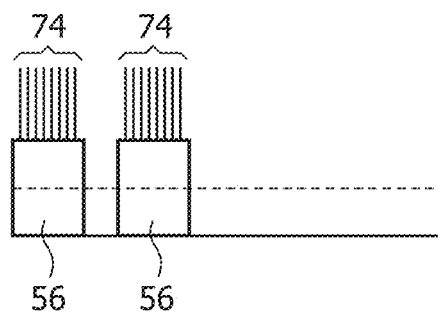

Another embodiment is shown in FIGS. 7-10. In this embodiment, a dental appliance 50 includes an actuator rod 52 which extends from an actuator 53. The actuator rod 52 engages a plurality of actuator sections 56-56 (FIGS. 8 and 9). The number of actuator sections for a particular appliance may vary; however, a typical number will be seven. Usually, four will be necessary for effective cleaning, although in some circumstances, a fewer number will be sufficient. Referring to FIGS. 8 and 9, the individual actuator sections are made of a hard plastic, such as ABS plastic, and are fixedly mounted on an elastic actuator rod 52. Actuator rod 52 is in the form of a flexible elastic tube or hose, having a diameter at rest of approximately 2 mm.

In operation, actuator 53 operates on the elastic actuator rod, such that it alternately expands from a rest position and then contracts back to its rest position, at a selected frequency, such as for example in the range of 100-300 Hz, like the previous embodiment. During expansion, the diameter of the elastic rod increases approximately 200 microns before returning to a neutral position, although this amount can vary. This increase and decrease in diameter of the actuator rod forces an outward opposing expansion of each actuator section 56 about the actuator rod.

The expansion action of the actuator sections is due to their particular configuration, shown most clearly in FIGS. 8 and 9. Each actuator section is generally in the overall shape of an oval, including a lower base portion 58 with an upper surface 60. Connecting the opposing edges 61, 62 of lower base portion 58 is a narrow curved bridge member 63. In the embodiment shown, the actuator sections are each approximately 12.5 mm long, 10 mm high and 3 mm thick (front to back). Bridge member 63 is approximately 0.5 mm wide (top to bottom), except for three hinge sections 66, 68 and 70 which are located, respectively, at opposing ends of bridge member 63 (where they meet the lower base portion 58) and at a mid-point of bridge member 63. Each of the hinge sections is approximately 0.2 mm wide.

Extending from upper surface 72 of each bridge member 63 are a plurality of bristle tufts 74. The bristle tufts can vary in number, but a typical number will be in the range of 12, while each bristle tuft will contain approximately 90 individual bristles, for example. The individual bristles can vary in size and configuration, but are typical bristles for cleaning teeth, i.e. approximately 8 mm long and 6 mil in diameter.

The lower section 58, besides having an opening 70 therein for the actuator rod, includes a slot 76 which extends downwardly from opening 70 to the edge of lower section 58. Positioned above opening 70 is another opening 78 which comprises two oval-like sections which extend from opposite sides of the center line of the lower section. A narrow slot 80 connects opening 70 to opening 78. Positioned between opening 78 and the upper surface 60 of lower section 58 is an additional small circular opening 82. On opposite sides of opening 82 are two narrow hinge portions 86 and 88, each approximately 1 mm wide (top to bottom).

In operation, as actuator rod 52 expands and contracts due to the operation of actuator 53, two mirror-image portions 84, 85 of lower section 58 move slightly outwardly, away from each other, about hinge portions 86 and 88. This causes an up/down movement of bridge member 63 because of hinge sections 66, 68 and 70 therein, producing a corresponding up/down movement of bristle tufts 74 toward and away from the teeth. This is a tapping/slight hammering action which produces cleaning of the teeth.

The above motion of the bridge member 63 relative to the expansion of the actuator rod is referred to as an amplification factor, i.e. the relatively small expansion of the actuator rod produces an amplified (larger) movement of the bristle tufts. An amplification factor (ratio) of at least seven and up to 40 is possible with the structure shown. As one example, a 0.25 mm expansion of the actuator rod results in a 1 mm stroke of the bristle tufts. Thus, an important concept in this embodiment is that a relatively small expansion of an actuator rod element can produce an effective bristle tuft stroke length.

Accordingly, embodiments have been disclosed which provide an effective bristle tuft action with either a relatively short bristle tuft stroke and/or a small movement of an actuator element can produce effective tapping/cleaning action of bristle tufts, directly toward and away from the teeth.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A dental cleaning appliance, comprising:
   an appliance body (14) having a brushhead portion (12) with a plurality of movable piston members (16) mounted therein for in-and-out movement thereof toward and away from the teeth when a distal end of the brushhead portion is positioned in the mouth;
   bristle tufts (20) mounted on the piston members, for cleaning contact with the teeth;
   a low frequency actuator (40) for moving the piston members at a low frequency to generally sequentially conform tips of the bristle tufts to the teeth; and
   a higher frequency actuator (42) for moving the piston members at a higher frequency relative to the teeth, the higher frequency movement of the piston members superimposed on the low frequency movement thereof, to produce cleaning of the teeth by periodic contact between the bristle tufts and the teeth.

2. The dental-cleaning appliance of claim 1, wherein the bristle cleaning action is a tapping action against the teeth.

3. The dental cleaning appliance of claim 1, wherein the higher frequency is at least 30 times greater than the low frequency.

4. The dental cleaning appliance of claim 1, wherein the low frequency is in the range of 1-6 Hz, and the higher frequency is in the range of 100-300 Hz.

5. The dental cleaning appliance of claim 1, wherein the brushhead includes a low frequency fluid flow channel (22) and a higher frequency fluid flow channel (24) for actuating the piston members, wherein the low frequency actuator moves fluid primarily into the low frequency flow channel through a narrow entrance (28), and the higher frequency actuator moves fluid into the higher frequency flow channel through a wider entrance (30).

6. The dental cleaning appliance of claim 5, wherein the low frequency actuator is a spring member and wherein the higher frequency actuator is a linear actuator/piston assembly.

7. The dental cleaning appliance of claim 6, wherein the higher frequency actuator is mounted on the spring member.

8. A dental cleaning appliance, comprising:
an appliance body (50), including a driving system (53) having an elastic elongated actuator member (52) which expands and contracts laterally about its longitudinal axis at a selected frequency;
a plurality of separate actuator sections (56), independent of each other and individually fixedly mounted on the actuator member which extends through an opening in the actuator sections, each actuator section having a lower base portion and an upper bridge portion, with an open area therebetween, being configured so that as the actuator member expands, the upper bridge portion (63) of the actuator section moves upwardly; and
bristle tufts (74) mounted on the upper portion of each actuator section such that as the actuator member expands, the upper portion of the actuator section and the bristle tufts mounted thereon move alternately outwardly and then back, toward and away from the teeth when the appliance is positioned in the mouth.

9. The dental cleaning appliance of claim 8, wherein the bristle tufts move a distance at least seven times the amount of the expansion of the actuator member.

10. The dental cleaning appliance of claim 8, wherein the bristle tufts move a distance approximately 40 times the expansion of the actuator member.

11. The dental cleaning appliance of claim 8, wherein the base portion includes a slot (76) which extends from a first opening (70) therein, through which opening the actuator member extends, to an edge of the base portion of the actuator section and further includes hinge portions (86,88) on the base portion on opposing sides of the center line of the actuator section above the first opening, and wherein the bridge section includes three hinge portions (66,68,70), one at each end thereof where the bridge portion joins the base portion, and one approximately at a center point of the bridge portion, such that as the actuator member expands in diameter, two parts (84,85) of the base portion move away from each other about the base portion hinge portions, forcing the bridge portion upwardly along with the bristle tufts mounted thereon.

12. The dental cleaning appliance of claim 11, wherein the actuator sections are oval in outline.

13. The dental cleaning appliance of claim 11, wherein the base portion includes a second opening (78) above the first opening, symmetrical about a center line of the actuator section, the base portion of the actuator section further including a third opening (82) between the second opening and an upper surface of the base portion, wherein the first and second hinge portions are defined partially by the second opening and are on opposite sides of said third opening.

14. The dental cleaning appliance of claim 8, wherein the frequency of movement of the actuator member and the bristle tufts is within the range of 100-300 Hz.

15. The dental cleaning appliance of claim 8, wherein the actuator sections are made from a hard plastic.

* * * * *